(12) United States Patent
Akazawa

(10) Patent No.: US 10,088,434 B2
(45) Date of Patent: Oct. 2, 2018

(54) INSPECTION SYSTEM AND INSPECTION METHOD

(71) Applicant: FUJITSU LIMITED, Kawasaki-shi, Kanagawa (JP)

(72) Inventor: Toshinobu Akazawa, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 15/697,482

(22) Filed: Sep. 7, 2017

(65) Prior Publication Data
US 2018/0100812 A1 Apr. 12, 2018

(30) Foreign Application Priority Data

Oct. 12, 2016 (JP) .................................. 2016-201153

(51) Int. Cl.
G01N 21/00 (2006.01)
G01N 21/94 (2006.01)
G01M 11/00 (2006.01)
G01N 21/952 (2006.01)
G01N 21/896 (2006.01)
G01N 21/95 (2006.01)

(52) U.S. Cl.
CPC ............. *G01N 21/94* (2013.01); *G01M 11/35* (2013.01); *G01M 11/37* (2013.01); *G01N 21/896* (2013.01); *G01N 21/952* (2013.01); *G01N 2021/9511* (2013.01); *G06T 2207/10152* (2013.01)

(58) Field of Classification Search
CPC ........... G01M 11/3145; G01M 11/335; G01M 11/33; G01M 11/3109; G01M 11/338

USPC ........................................................ 356/73.1
See application file for complete search history.

(56) References Cited

U.S. PATENT DOCUMENTS

| 4,508,453 A * | 4/1985 | Hara ..................... G01N 21/956 348/126 |
| 5,748,299 A | 5/1998 | Esmaeili |
| 6,831,738 B2 * | 12/2004 | Rogers ............... G01N 21/9515 356/244 |
| 2002/0079434 A1 * | 6/2002 | Kimura .................... G01V 8/24 250/227.11 |
| 2003/0004412 A1 * | 1/2003 | Izatt ..................... A61B 5/0066 600/425 |

(Continued)

FOREIGN PATENT DOCUMENTS

| EP | 0485629 A1 * | 5/1992 | ............ G01M 11/33 |
| JP | 09-145542 | 6/1997 | |
| JP | 2015-510121 | 4/2015 | |

*Primary Examiner* — Md M Rahman
(74) *Attorney, Agent, or Firm* — Fujitsu Patent Center

(57) ABSTRACT

An inspection system includes a detection device arranged between a connector that couples a plurality of optical fibers to a port and the port; and a determination device that determines whether there is dart between the connector and the port, based on an output from the detection device, wherein the detection device includes a plurality of diodes that convert light that is output from each of the plurality of optical fibers to an electrical signal indicating intensity and distribution of the light, and the determination device includes a processor configured to determine whether there is dart between the connector and the port, based on the intensity and distribution of the light, which are indicated by the electrical signal.

13 Claims, 22 Drawing Sheets

(56) References Cited

U.S. PATENT DOCUMENTS

| | | | |
|---|---|---|---|
| 2003/0026567 A1* | 2/2003 | Cryan | B29D 11/00682 385/124 |
| 2003/0174319 A1* | 9/2003 | Buzzetti | G02B 6/3807 356/237.1 |
| 2003/0174875 A1* | 9/2003 | Buzzetti | G01M 11/081 382/141 |
| 2003/0202754 A1* | 10/2003 | Kato | G02B 6/4292 385/89 |
| 2004/0196459 A1* | 10/2004 | Cyr | G01N 21/31 356/344 |
| 2015/0009320 A1 | 1/2015 | Klein et al. | |
| 2017/0295336 A1* | 10/2017 | Kimura | H04N 5/378 |

* cited by examiner

INSPECTION SYSTEM AND INSPECTION METHOD

CROSS-REFERENCE TO RELATED APPLICATION

This application is based upon and claims the benefit of priority of the prior Japanese Patent Application No. 2016-201153, filed on Oct. 12, 2016, the entire contents of which are incorporated herein by reference.

FIELD

The embodiments discussed herein are related to an inspection system and an inspection method.

BACKGROUND

In some of networks used in parallel computers or the like, an optical cable is used for physically coupling a plurality of nodes with one another. There are cases in which a contaminant, such as dust or the like, enters between an optical cable and a connection unit of a rack of a computer. When a contaminant enters between the optical cable and the connection unit of the rack of the computer, the ratio at which the computer fails to receive data that has been transmitted via the optical cable increases. Thus, a link connection between nodes might be physically cut off (in other words, a link-down might occur). In some cases, even a contaminant having a size which it is not possible to visually detect causes reduction in transmission quality of a link, whereas, in other cases, reduction in the transmission quality occurs due to some other factor than a contaminant. Therefore, after the power of a part of a device, which is related to the link, is turned off, the optical cable is removed at both ends, and a port at a side surface of the device is cleaned, an operation of visually reviewing inside of a rear rack which is crowded with a cable, a water cooling kit, a power supply device, or the like, or like operation is performed. A contaminant attached to an end surface of the optical cable is removed using a special cleaner. For example, Japanese National Publication of International Patent Application No. 2015-510121, Japanese Laid-open Patent Publication No. 9-145542, or the like discusses related art.

Incidentally, after cleaning of the optical cable and visually reviewing of the inside of the rear rack have been performed, the optical cable is coupled to the computer again, the computer is started up, and whether or not the transmission quality has been improved is checked. The above-described operation considerably occurs in a site of a test, production, a product delivery destination, or the like of a parallel computer. The computer is started up after having gone through certain initialization processing, and therefore, it takes some time to start up the computer. Therefore, an operation of cleaning of the optical cable, visually reviewing of the rear rack, restarting up of the computer, or the like is a factor of increase in an operation time of a transmission test in a large-scale parallel computer. In view of the foregoing, it is preferable that reduction in operation time of a test of transmission between computers is enabled.

SUMMARY

According to an aspect of the invention, an inspection system includes a detection device arranged between a connector that couples a plurality of optical fibers to a port and the port; and a determination device that determines whether there is dart between the connector and the port, based on an output from the detection device, wherein the detection device includes a plurality of diodes that convert light that is output from each of the plurality of optical fibers to an electrical signal indicating intensity and distribution of the light, and the determination device includes a processor configured to determine whether there is dart between the connector and the port, based on the intensity and distribution of the light, which are indicated by the electrical signal.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

Embodiments of an inspection device and an inspection method disclosed herein will be described in detail below with reference to the accompanying drawings. A technology disclosed herein is not limited to the embodiments below.

First Embodiment

Figure 1:
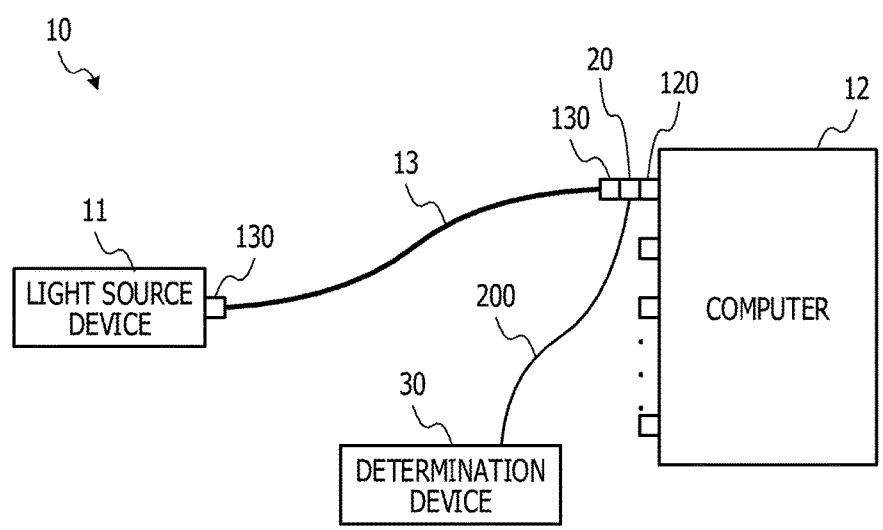
FIG. 1 is a block diagram illustrating an example of an inspection system.

FIG. 1 is a block diagram illustrating an example of an inspection system 10. The inspection system 10 according to a first embodiment includes a light source device 11, a detection device 20, and a determination device 30. The inspection system 10 according to the first embodiment is used, for example, in processing of checking connection between a cable 13 and a computer 12. The computer 12 is included in a parallel computer system, which includes a plurality of computers 12. In the parallel computer system, the computers 12 are coupled to one another via the cable 13, such as an optical fiber cable or the like. The plurality of computers 12 communicates with one another via the cable 13 and thus exhibits a function as the parallel computer system.

The light source device 11 is coupled to the cable 13 via a connector 130 provided at each of both ends of the cable 13 and transmits an optical signal to the cable 13. In the first embodiment, the cable 13 is a multi-core optical fiber cable including a plurality of optical fibers. The light source device 11 transmits an optical signal to each of the optical fibers in the cable 13.

The detection device 20 is configured such that one end of the detection device 20 is coupled to a connector 130 of the cable 13 and the other end thereof is coupled to a port 120 of the computer 12. The detection device 20 is coupled to the determination device 30 via a cable 200. The detection device 20 transmits an optical signal that has been output from the connector 130 to the port 120 through each of the optical fibers. Then, the detection device 20 outputs an electrical signal that indicates the intensity and distribution of light reflected on an end surface of the port 120 to the determination device 30 via the cable 200. The detection device 20 is an example of a reflection pattern detection unit.

The determination device 30 determines, based on the intensity and distribution of light that has been output from the detection device 20, whether or not there is a contamination, such as dust or the like, between the connector 130 and the port 120. The contamination is an example of dirt between the connector 130 and the port 120. The determination device 30 is an example of a determination unit. The inspection system 10 including the detection device 20 and the determination device 30 is an example of an inspection device.

Figure 2:
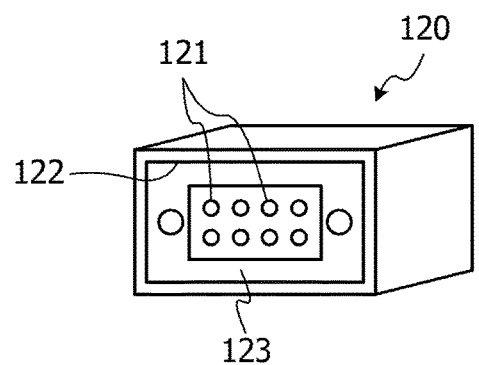
FIG. 2 is a view illustrating an example of a port.

FIG. 2 is a view illustrating an example of the port 120. The port 120 is provided on a side surface of the computer 12 and includes a base unit 123 including an end surface 121 of a transmission and reception unit that performs transmission or reception of an optical signal for each optical fiber and a housing 122 that accommodates the base unit 123.

Figure 3:
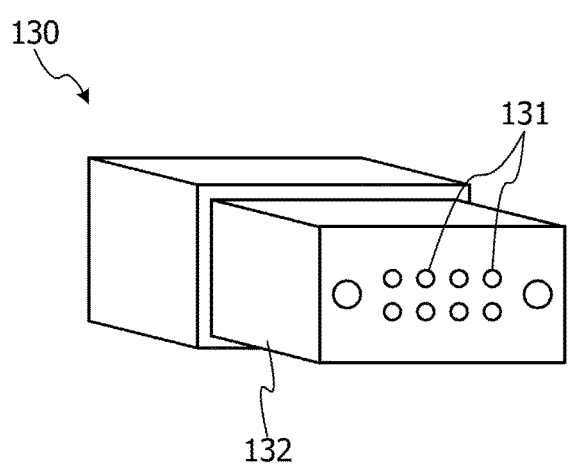
FIG. 3 is a view illustrating an example of a connector.

FIG. 3 is a view illustrating an example of the connector 130. The connector 130 includes a base unit 132 including an end surface 131 of each optical fiber through which an optical signal is transmitted or received for each optical fiber.

Figure 4:
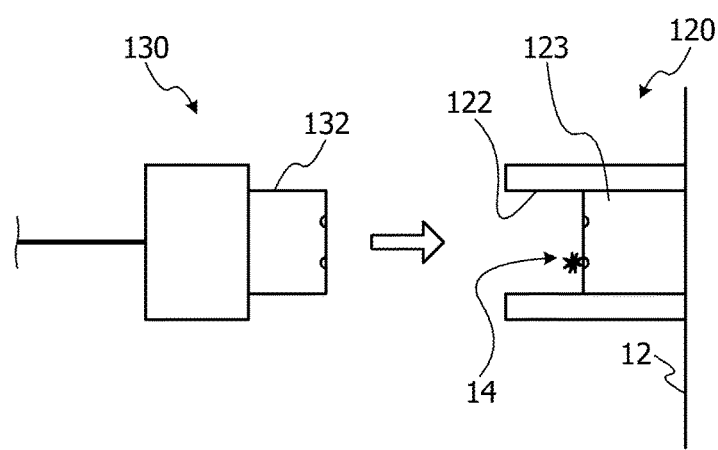
FIG. 4 is a view illustrating an example of connection of a connector and a port.

FIG. 4 is a view illustrating an example of connection of the connector 130 and the port 120. For example, as indicated by a white arrow in FIG. 4, the base unit 132 of the connector 130 is inserted in the housing 122 of the port 120, and thereby, the connector 130 and the port 120 are coupled to one another. In a state in which the connector 130 and the port 120 are coupled to one another, for each optical fiber, the end surface 131 and the end surface 121 are in surface contact with one another. Thus, the optical signal that has been output from the computer 12 is output to the cable 13 via the port 120 and the connector 130. Then, the output signal that has been transmitted via the cable 13 is input to the computer 12 via the connector 130 and the port 120.

There is a case, for example, as illustrated in FIG. 4, if there is a contamination 14, such as dust or the like, between the end surface 131 of the connector 130 and the end surface 121 of the port 120, an optical signal that is transmitted through the optical fiber is attenuated or scattered. Depending on the contamination 14, there is a case in which an optical signal transmitted through the optical fiber is sheltered. If the intensity of the optical signal that has been received at the port 120 of a light receiving unit of the computer 12 is less than certain intensity, the computer 12 fails reception of data by the optical signal. Then, in the computer 12, an error that indicates a failure of data reception is notified to an operator of the computer 12 or the like. The operator investigates a cause of the failure of data reception.

A possible cause of the failure of data reception is that the contamination 14 enters between the end surface 131 of the connector 130 and the end surface 121 of the port 120. Other possible causes of the failure of data reception include a disconnection of the optical fiber in the cable 13, a problem of a device in the computer 12, or the like. Therefore, it takes some time to investigate a cause of the failure.

Figure 5:
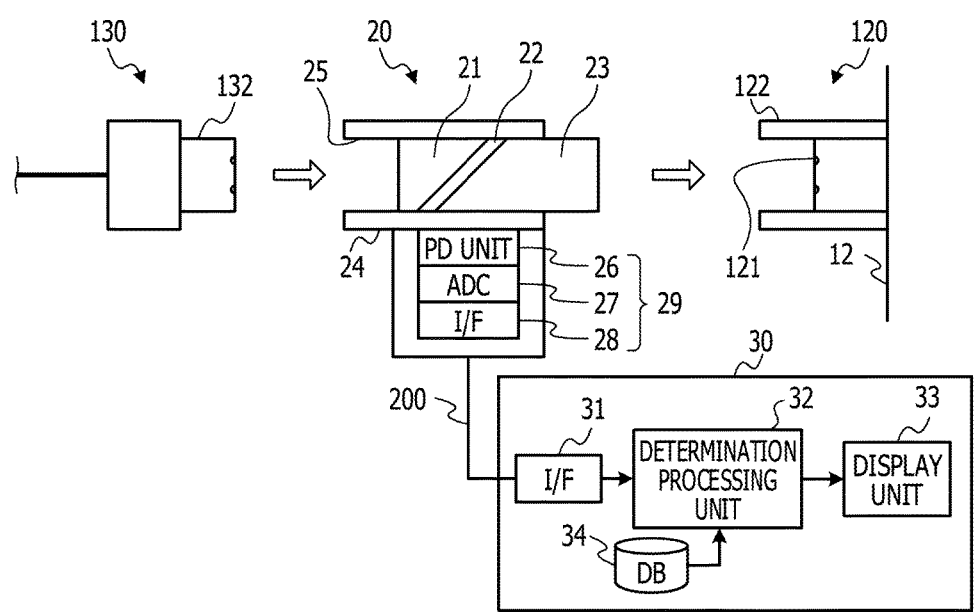
FIG. 5 is a view illustrating an example of connection of a connector and a port via a detection device.

In contrast, in the inspection system 10 of the first embodiment, when coupling of the connector 130 of the cable 13 and the port 120 of the computer 12 to one another is performed, for example, as illustrated in FIG. 5, the detection device 20 is inserted between the connector 130 and the port 120. Then, the determination device 30 determines, based on an electrical signal that corresponds to an optical signal that is output from the detection device 20 and is transmitted through the optical fiber, whether or not there is the contamination 14 between the connector 130 and the port 120. If it is determined by the determination device 30 that there is the contamination 14 between the connector 130 and the port 120, the end surface 131 of the connector 130 and the end surface 121 of the port 120 are cleaned, and then, are coupled to one another again. Thus, in an operation of investigating a cause of the failure of data reception, an operation of checking whether or not there is the contamination 14 between the connector 130 and the port 120 may be omitted and thus an operation time spent for investigating a cause of the failure of data reception may be reduced.

Next, with reference to FIG. 5, a structure of the detection device 20 will be described. FIG. 5 is a view illustrating an example of connection of the connector 130 and the port 120 via the detection device 20. The detection device 20 includes, for example, as illustrated in FIG. 5, a light guide unit 21, a reflection unit 22, a light guide unit 23, and an output unit 29. The output unit 29 includes a photodiode (PD) unit 26, an analog to digital converter (ADC) 27, and an interface (I/F) 28.

For example, as indicated by white arrows in FIG. 5, the base unit 132 of the connector 130 is inserted in a recess 25 formed by a housing 24 and the light guide unit 21 of the detection device 20 and the light guide unit 23 is inserted in the housing 122 of the port 120. Thus, the connector 130 and the port 120 are coupled to one another via the detection device 20.

Each of the light guide unit 21, the reflection unit 22, and the light guide unit 23 is formed of a material that transmits light. The reflection unit 22 is formed of a material that transmits light and has a different refractive index from that of the material of each of the light guide unit 21 and the light guide unit 23. The reflection unit 22 is arranged between the light guide unit 21 and the light guide unit 23 so as to be oblique relative to a path of an optical signal that enters the port 120 from each optical fiber in the connector 130. The reflection unit 22 may be a gas that exists in a gap that is formed so as to be oblique between the light guide unit 21 and the light guide unit 23. In the first embodiment, each of the light guide unit 21 and the light guide unit 23 is, for example, quartz glass. The reflection unit 22 is air. Each of the light guide unit 21 and the light guide unit 23 may be formed of some other material, such as crystal or the like, as long as each of the light guide unit 21 and the light guide unit 23 is formed of a material that transmits light. The reflection unit 22 may be formed of a material, such as crystal, quartz glass, or the like, as long as the reflection unit 22 is formed of a material that transmits light and has a different refractive index from that of the material of each of the light guide unit 21 and the light guide unit 23.

Figure 6:
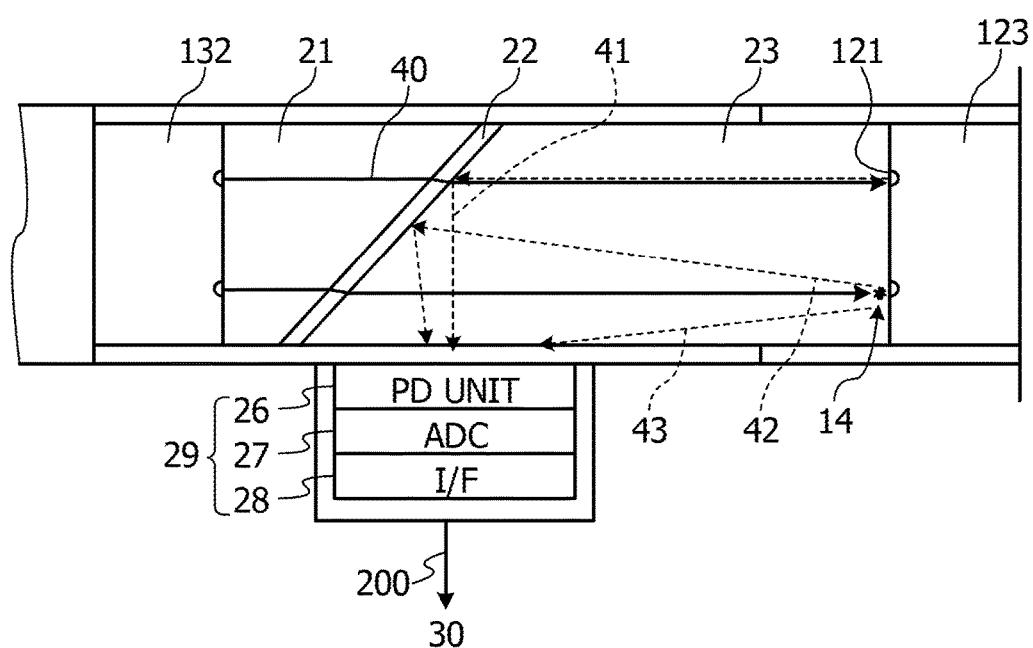
FIG. 6 is a view illustrating an example of reflected light.

FIG. 6 is a view illustrating an example of reflected light. For example, as illustrated in FIG. 6, in a state in which the connector 130 and the port 120 are coupled to one another via the detection device 20, light from each optical fiber, which has been output from the base unit 132 in the connector 130, is transmitted through the light guide unit 21 and enters the reflection unit 22, for example, as indicated by an arrow 40. Light that has entered the reflection unit 22 is refracted on a boundary surface of the light guide unit 21 and the reflection unit 22 and a boundary surface of the reflection unit 22 and the light guide unit 23 and enters the end surface 121 of the port 120. Then, a part of the light that has entered the end surface 121 of the port 120 is reflected on the end surface 121 and enters the reflection unit 22 again. Then, a part of the light that has entered the reflection unit 22 is reflected on the boundary surface between the light guide unit 23 and the reflection unit 22. Then, the reflected light enters the PD unit 26, for example, along a path indicated by a broken line arrow 41 in FIG. 6.

On the other hand, if there is the contamination 14 in the end surface 121 of the port 120, the entire part or a part of light that has entered the end surface 121 of the port 120 is reflected or scattered by the contamination 14. Then, the light reflected or scattered by the contamination 14 enters the reflection unit 22 again along a different path from a path when there is not the contamination 14, for example, as indicated by a broken line arrow 42 in FIG. 6. Therefore, a part of the light that has entered the reflection unit 22 is reflected on the boundary surface of the light guide unit 23 and the reflection unit 22. Then, the reflected light enters a different location from a location in the PD unit 26, which light enters when there is not the contamination 14. There is also a case in which the light reflected or scattered by the contamination 14 does not enter the reflection unit 22 but directly enters the PD unit 26, for example, as indicated by a broken line arrow 43 in FIG. 6. The light reflected or scattered by the contamination 14 enters the PD unit 26 with different intensity from the intensity of light that enters the PD unit 26 when there is not the contamination 14. For example, the entire reflected light that is reflected by the contamination 14 has higher intensity than the intensity of light that enters the PD unit 26 when there is not the contamination 14. Light scattered by the contamination 14 has lower intensity than the intensity of light that enters the PD unit 26 when there is not the contamination 14. Therefore, based on the location and intensity of light that has entered the PD unit 26, whether or not there is the contamination 14 may be determined.

Figure 7:
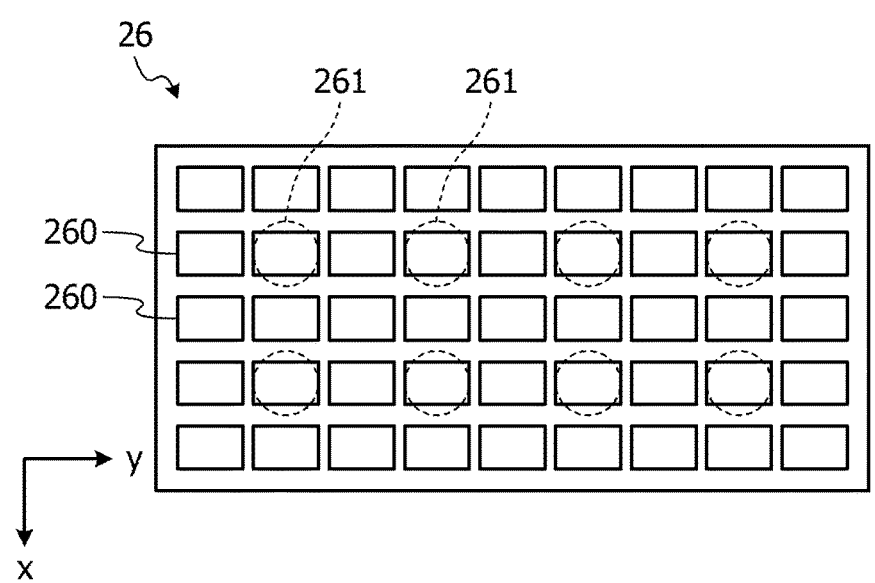
FIG. 7 is a view illustrating an example of an arrangement of photodiodes (PDs) in a first embodiment.

In the first embodiment, for example, as illustrated in FIG. 7, the PD unit 26 includes a plurality of PDs 260 arranged in arrays. FIG. 7 is a view illustrating an example of an arrangement of the PDs 260 in the first embodiment. In the first embodiment, for example, as illustrated in FIG. 7, a plurality of arrays each including multiple ones of the PDs 260 which are arranged in line in certain intervals in a y direction in FIG. 7 are arranged in certain intervals in an x direction in FIG. 7. The y direction is an example of a first direction. The x direction is an example of a second direction. Each of the PDs 260 converts light quantity to an electrical signal. The PD 260 is an example of a converter. The electrical signal that has been converted in each PD 260 is an electrical signal that corresponds to the intensity of light that has been received in each location in which each PD 260 is arranged. For example, as illustrated in FIG. 7, the PDs 260 are arranged such that at least one of the PDs 260 is located in a location including an area 261 that light from each optical fiber, which has been reflected by the reflection unit 22, enters when there is not the contamination 14 between the connector 130 and the port 120. Thus, in each PD 260, when there is not the contamination 14 between the connector 130 and the port 120, an electrical signal that indicates light quantity of a certain magnitude is output. By referring to an electrical signal that has been output from each PD 260, whether or not there is the contamination 14 between the connector 130 and the port 120 is determined.

Figure 8:
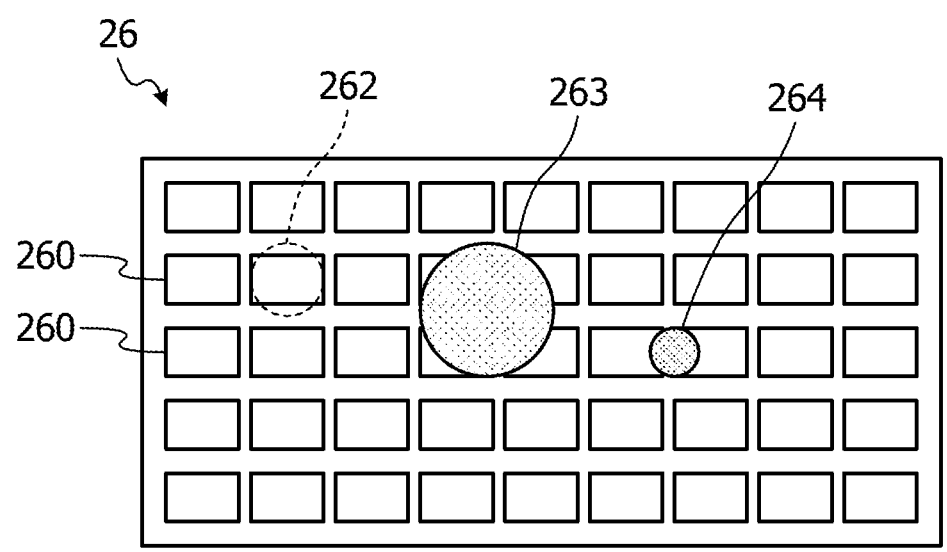
FIG. 8 is a view illustrating an example of distribution of reflected light when there is a contamination.

In the first embodiment, for example, as illustrated in FIG. 7, the PDs 260 are arranged such that at least one of the PDs 260 is located in a location other than the location including the area 261 that light from each optical fiber, which has been reflected by the reflection unit 22, enters when there is not the contamination 14. For example, as illustrated in FIG. 8, there is a case in which, when there is the contamination 14, light from each optical fiber, which has been reflected by the reflection unit 22, is scattered in an area 263 that is larger than an area 262 that the light enters when there is not the contamination 14. There is a case in which, for example, as illustrated in FIG. 8, when there is the contamination 14, light from each optical fiber, which has been reflected by the reflection unit 22, enters an area 264 located in a different location from that of the area 262 that light enters when there is not the contamination 14. The PD 260 is located in a location other than the location including the area 261 that light from each optical fiber, which has been reflected by the reflection unit 22 when there is not the contamination 14, enters, and thereby, determination accuracy when there is the contamination 14 may be increased.

Figure 9:
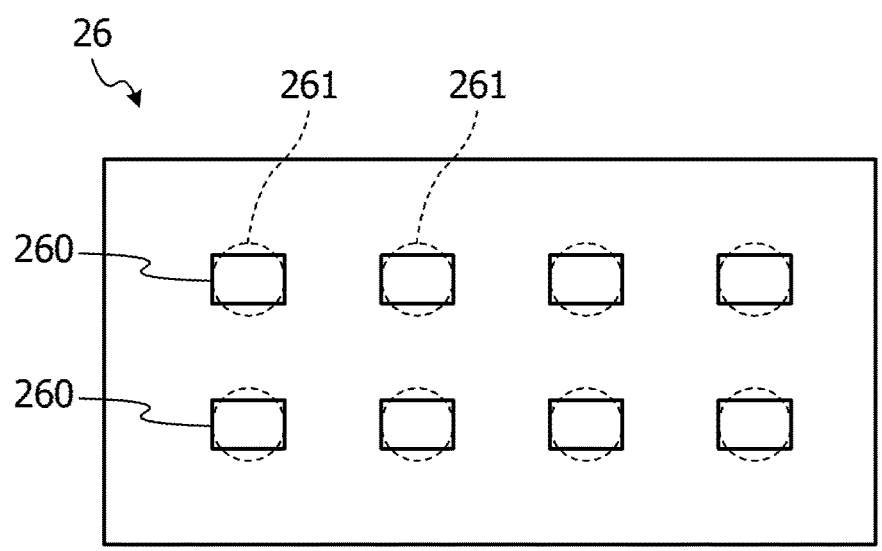
FIG. 9 is a view illustrating another example of an arrangement of PDs in the first embodiment.

For example, as illustrated in FIG. 9, there may be a case in which the PD 260 is not located in a location other than the location including the area 261 that light from each optical fiber, which has been reflected by the reflection unit 22 when there is not the contamination 14 between the connector 130 and the port 120, enters. Thus, the number of the PDs 260 may be reduced and costs of the detection device 20 may be reduced.

Returning to FIG. 5, the description will continue. The ADC 27 converts an electrical signal that has been output from each PD 260 in the PD unit 26 from an analog signal to a digital signal. The I/F 28 outputs the electrical signal that has been converted to a digital signal by the ADC 27 to the determination device 30 via the cable 200, such as a local area network (LAN) cable or the like.

For example, as illustrated in FIG. 5, the determination device 30 includes an I/F 31, a determination processing unit 32, a display unit 33, and a DB 34. The I/F 31 receives an electrical signal that has been output from the detection device 20 via the cable 200 and outputs the electrical signal to the determination processing unit 32. Data that indicates the value of an electrical signal of each PD 260 when there is not the contamination 14 between the connector 130 and the port 120 is stored in the DB 34 in advance. Data that indicates a threshold used for determining whether or not there is the contamination 14 between the connector 130 and the port 120 is stored in the DB 34 in advance.

The determination processing unit 32 acquires an electrical signal that has been output from each PD 260 via the cable 200 and the I/F 31. Then, the determination processing unit 32 determines, based on the acquired electrical signal of each PD 260, whether or not there is the contamination 14 between the connector 130 and the port 120. In the first embodiment, the determination processing unit 32 calculates, for example, for each PD 260, a difference between the value of an electrical signal output from the detection device 20 and the value of an electrical signal stored in the DB 34. Then, if a value calculated from the sum of the differences that have been calculated for the PDs 260 is a predetermined threshold or more, the determination processing unit 32 determines that there is the contamination 14 between the connector 130 and the port 120. Specifically, the determination processing unit 32 calculates a Euclidean distance $L_e$, for example, based on Expression 1 below.

[Expression 1]

$$L_e = \sqrt{\sum_{i=1}^{N} (REF_i - IN_i)^2} \quad (1)$$

In Expression 1, REF, represents the value of an electric signal of an ith PD 260 that is stored in the DB 34. $IN_i$ represents the value of an electrical signal of an ith PD 260 that has been output from the detection device 20. In Expression 1, N represents the total number of the PDs 260 arranged in the PD unit 26.

Then, the determination processing unit 32 determines whether or not the Euclidean distance $L_e$ that has been calculated using Expression 1 is a threshold stored in the DB 34 or more. If the Euclidean distance $L_e$ is the threshold or more, the determination processing unit 32 determines that there is the contamination 14 between the connector 130 and the port 120. On the other hand, if the Euclidean distance $L_e$ is less than the threshold, the determination processing unit 32 determines that there is not the contamination 14 between the connector 130 and the port 120.

The display unit 33 is, for example, a display and notifies an operator of the inspection system 10 or the like of a determination result of determination performed by the determination processing unit 32. The display unit 33 may be configured to transmit the determination result of determination performed by the determination processing unit 32 to another device via a communication line.

In the first embodiment, also when there is a crack in an optical fiber in the cable 13 or the optical fiber is disconnected, the determination processing unit 32 determines that there is the contamination 14 between the connector 130 and the port 120. In this case, cleaning between the connector 130 and the port 120 is performed, and then, a connection check is performed again. Even thereafter, if it is determined by the determination device 30 that there is the contamination 14 between the connector 130 and the port 120, exchange of the cable 13 is performed.

The determination processing unit 32 may be configured to calculate a manhattan distance $L_m$, for example, based on Expression 2 below, and determine whether or not there is the contamination 14, based on comparison between the calculated manhattan distance $L_m$ and a threshold stored in the DB 34.

[Expression 2]

$$L_m = \sum_{i=1}^{N} |REF_i - IN_i| \quad (2)$$

Figure 10:
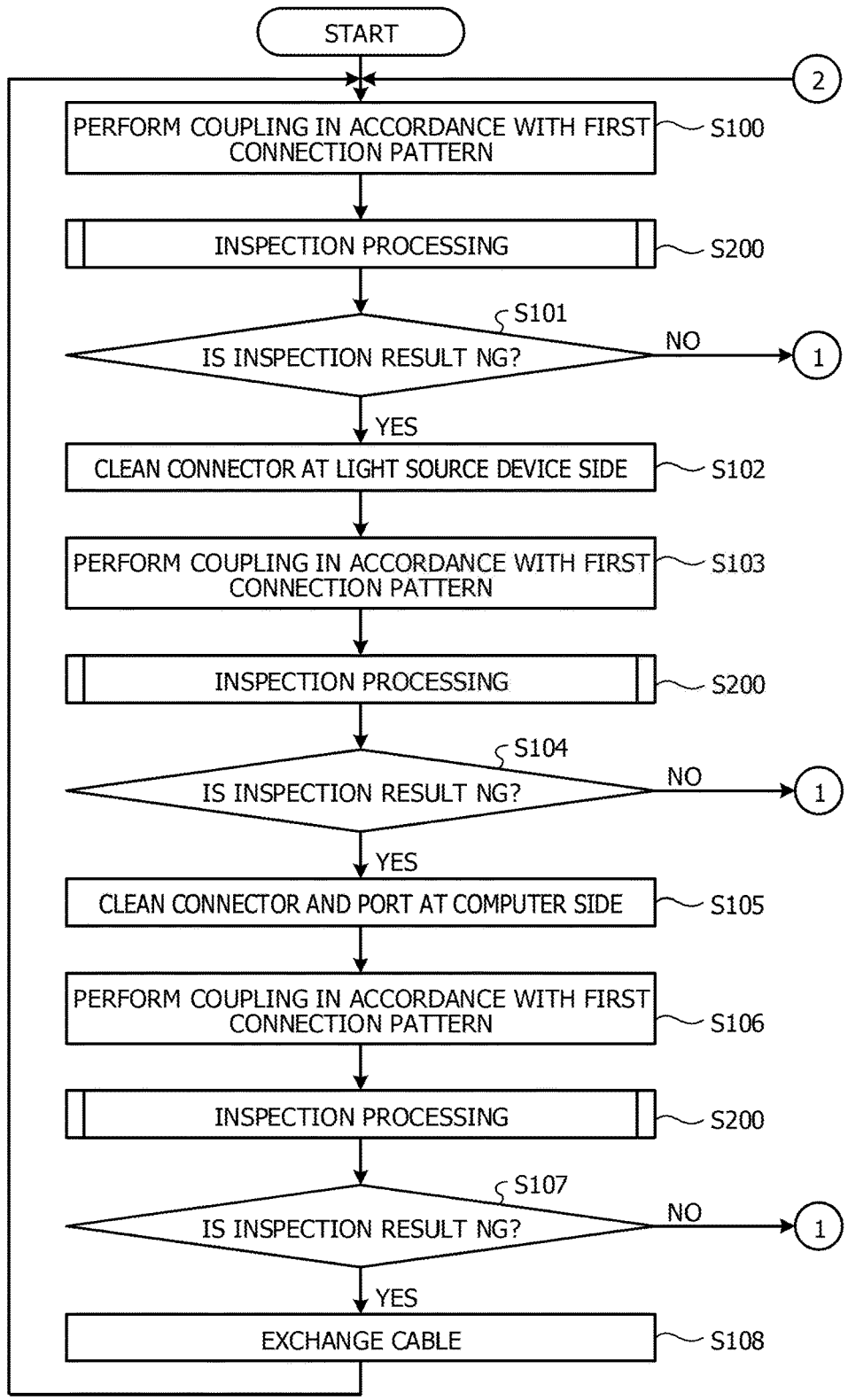
FIG. 10 is a flowchart illustrating an example of connection check processing.
Figure 11:
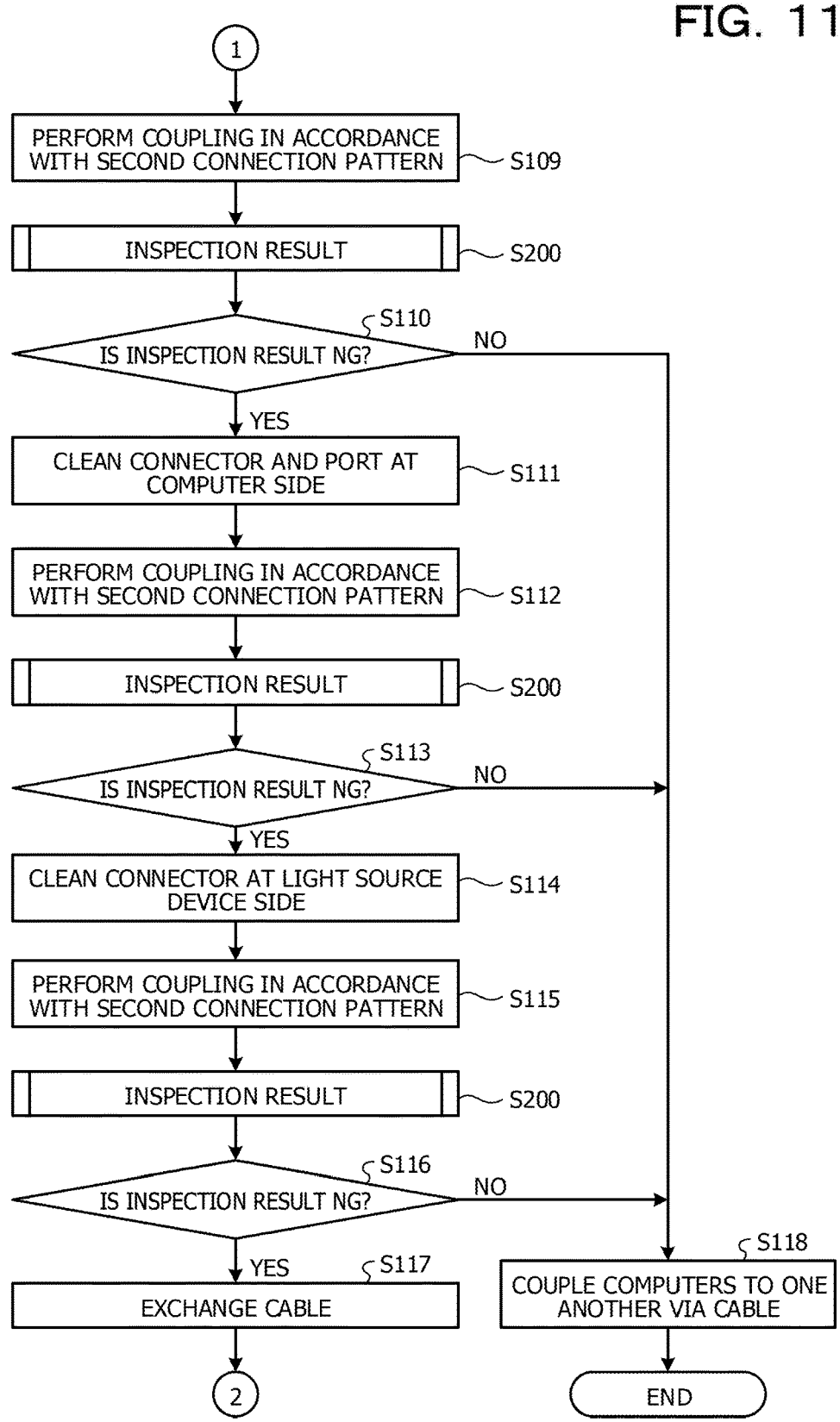
FIG. 11 is a flowchart illustrating an example of connection check processing.

FIG. 10 and FIG. 11 are flowcharts illustrating an example of connection check processing. The connection check processing illustrated in FIG. 10 and FIG. 11 is processing that is performed when coupling of the cable 13 to the computer 12 is performed. The connection check processing illustrated in FIG. 10 and FIG. 11 is performed, for example, for connections illustrated in FIG. 12A and FIG. 12B. The connection illustrated in FIG. 12A will be hereinafter referred to as a first connection pattern and the connection illustrated in FIG. 12B will be hereinafter referred to as a second connection pattern. The connection check processing illustrated in FIG. 10 and FIG. 11 is performed using the light source device 11, but the technology disclosed herein is not limited thereto. For example, without using the light source device 11, but using light output from the computer 12 coupled to one end of the cable 13, connection check processing may be performed for the computer 12 coupled to the other end of the cable 13.

Figure 12A:
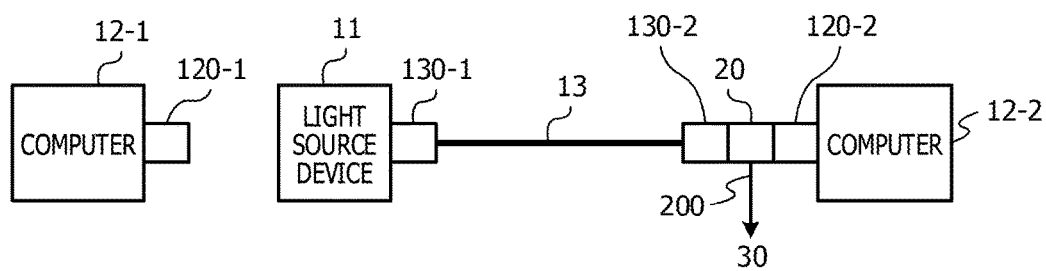
FIGS. 12A and 12B are views each illustrating an example of connection when connection check processing is performed.

First, the light source device 11, the cable 13, the detection device 20, and a computer 12-2 are coupled in accordance with the first connection pattern (S100). In the first connection pattern, for example, as illustrated in FIG. 12A, the light source device 11 and the cable 13 are coupled to one another via a connector 130-1 and the cable 13 and the detection device 20 are coupled to one another via a connector 130-2. The detection device 20 and the computer 12-2 are coupled to one another via a port 120-2 and the detection device 20 is coupled to the determination device 30 via the cable 200.

Figure 13:
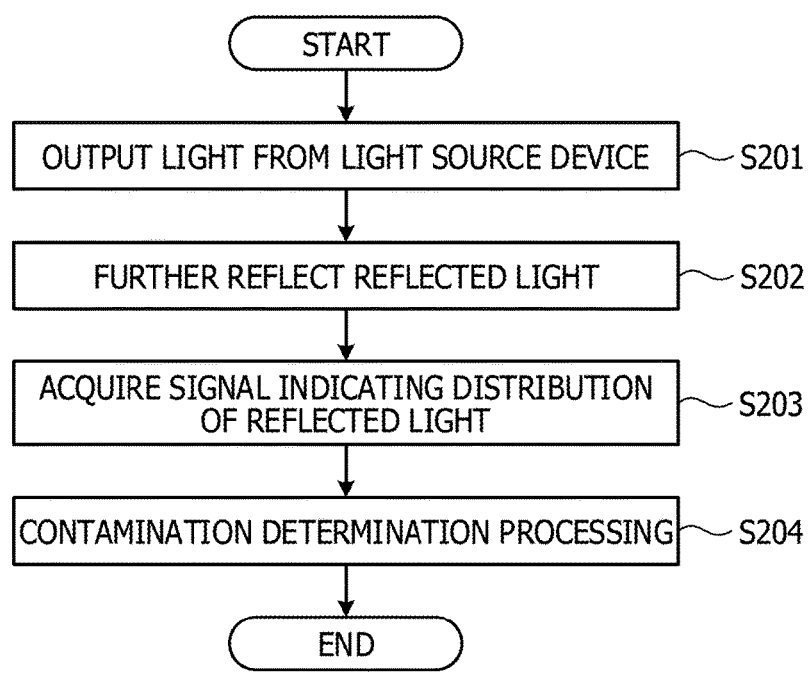
FIG. 13 is a flowchart illustrating an example of inspection processing in the first embodiment.

Next, inspection processing is executed by the inspection system 10 (S200). FIG. 13 is a flowchart illustrating an example of inspection processing in the first embodiment. In the inspection processing in the first embodiment, for example, as illustrated in FIG. 13, light is output from the light source device 11 (S201). Light that has been output from the light source device 11 enters the cable 13 via the connector 130, is transmitted through each of the optical fibers in the cable 13, and enters the detection device 20 from the connector 130.

As illustrated in FIG. 6, the light that has entered the detection device 20 is transmitted through the detection device 20 and is reflected by the port 120, and reflected light that has been reflected by the port 120 is further reflected by the reflection unit 22 in the detection device 20 and enters the PD unit 26 (S202).

Reflected light of each optical fiber, which has entered the PD unit 26, is converted to an electrical signal that corresponds to light quantity by the corresponding one of PDs 260. An analog electrical signal that has been converted by each PD 260 is converted to a digital electrical signal by the ADC 27 and thus is output to the determination device 30 via the cable 200 by the I/F 28.

The determination device 30 acquires an electrical signal of each PD 260, which has been output from the detection device 20 via the cable 200 (S203). Then, the determination device 30 executes determination processing of determining whether or not there is the contamination 14 between the connector 130 and the port 120, based on the value of the electrical signal of each PD 260 (S204). Specifically, the determination processing unit 32 of the determination device 30 determines whether or not the Euclidean distance $L_e$ that has been calculated, based on Expression 1 described above, is the threshold stored in the DB 34 or more. If the Euclidean distance $L_e$ is the threshold or more, the determination processing unit 32 determines that there is the contamination 14 between the connector 130 and the port 120. If the determination processing unit 32 determines that there is the contamination 14 between the connector 130 and the port 120, the determination processing unit 32 displays an inspection result as NG (no good) on the display unit 33. On the other hand, if the Euclidean distance $L_e$ is less than the threshold, the determination processing unit 32 determines that there is not the contamination 14 between the connector 130 and the port 120. If the determination processing unit 32 determines that there is not the contamination 14 between the connector 130 and the port 120, the determination processing unit 32 displays an inspection result as OK on the display unit 33.

Returning to FIG. 10, the description will continue. After the inspection processing ends, whether or not the inspection result of the inspection processing is NG, that is, whether or not there is the contamination 14 between the connector 130 and the port 120, is determined (S101). If the inspection result is not NG (NO in S101), processing illustrated in S109 in FIG. 11 is executed.

On the other hand, if the inspection result is NG (YES in S101), in the first connection pattern illustrated in FIG. 12A, the end surface 131 of the connector 130-1 at the light source device 11 side is cleaned (S102). Then, the light source device 11, the cable 13, the detection device 20, and the computer 12-2 are coupled to one another again in accordance with the first connection pattern (S103) and inspection processing illustrated in S200 is executed again.

Next, after the inspection processing ends, whether or not the inspection result of the inspection processing is NG is determined (S104). If the inspection result is not NG (NO in S104), the processing illustrated in S109 in FIG. 11 is executed.

On the other hand, if the inspection result is NG (YES in S104), in the first connection pattern illustrated in FIG. 12A, the end surface 131 of the connector 130-2 at the computer 12-2 side and the end surface 121 of the port 120-2 of the computer 12-2 are cleaned (S105). Then, the light source device 11, the cable 13, the detection device 20, and the computer 12-2 are coupled to one another again in accordance with the first connection pattern (S106) and the inspection processing illustrated in S200 is executed again.

Next, after the inspection processing ends, whether or not the inspection result of the inspection processing is NG is determined (S107). If the inspection result is not NG (NO in S107), the processing illustrated in S109 in FIG. 11 is executed. On the other hand, if the inspection result is NG (YES in S107), the cable 13 is exchanged (S108) and processing illustrated in S100 is executed again.

Figure 12B:
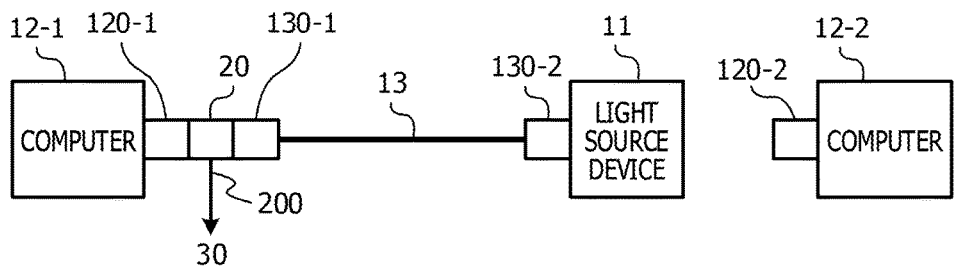

In S101, S104, and S107, if the inspection result of the inspection processing is not NG, the light source device 11, the cable 13, the detection device 20, and the computer 12-1 are coupled to one another in accordance with the second connection pattern (S109). In the second connection pattern, for example, as illustrated in FIG. 12B, the light source device 11 and the cable 13 are coupled to one another via the connector 130-2 and the cable 13 and the detection device 20 are coupled to one another via the connector 130-1. The detection device 20 and the computer 12-1 are coupled to one another via the port 120-1 and the detection device 20 is coupled to the determination device 30 via the cable 200.

Next, the inspection processing illustrated in S200 is executed again. Then, after the inspection processing ends, whether or not the inspection result of the inspection processing is NG is determined (S110). If the inspection result is not NG (NO in S110), processing illustrated in S118 is executed.

ON the other hand, if the inspection result is NG (YES is S110), in the second connection pattern illustrated in FIG. 12B, the end surface 131 of the connector 130-1 at the computer 12-1 side and the end surface 121 of the port 120-1 of the computer 12-1 are cleaned (S111). Then, the light source device 11, the cable 13, the detection device 20, and the computer 12-1 are coupled to one another in accordance with the second connection pattern again (S112) and the inspection processing illustrated in S200 is executed again.

Next, after the inspection result ends, whether or not the inspection result of the inspection processing is NG is determined (S113). If the inspection result is not NG (NO in S113), the processing illustrated in S118 is executed.

On the other hand, if the inspection result is NG (YES in S113), in the second connection pattern illustrated in FIG. 12B, the end surface 131 of the connector 130-2 at the light source device 11 side is cleaned (S114). Then, the light source device 11, the cable 13, the detection device 20, and the computer 12-1 are coupled to one another in accordance with the second connection pattern again (S115) and the inspection processing illustrated in S200 is executed again.

Next, after the inspection processing ends, whether or not the inspection result of the inspection processing is NG is determined (S116). If the inspection result is not NG (NO in S116), the detection device 20 is removed. Then, the computer 12-1 and the computer 12-2 are coupled to one another via the cable 13 (S118) and the connection check processing illustrated in this flowchart ends. On the other hand, if the inspection result is NG (YES in S116), the cable 13 is exchanged (S117) and the processing illustrated in S100 is executed again.

As is evident from the description above, the inspection system 10 of the first embodiment includes the detection device 20 and the determination device 30. The detection device 20 includes the light guide unit 21, the reflection unit 22, the light guide unit 23, and the output unit 29. The light guide unit 21 and the light guide unit 23 transmit light that has been output from each of the plurality of optical fibers to the corresponding port 120 of the computer 12. The reflection unit 22 further reflects light that has been transmitted through the light guide unit 21 and the light guide unit 23 and has been reflected by the port 120. The output unit 29 includes the plurality of PDs 260 that convert light quantity to an electric signal, and outputs, by the corresponding PD 260, the light quantity of each light that has been reflected by the reflection unit 22 as an electrical signal in the corresponding one of locations in which the PDs 260 are located to the determination device 30. The determination device 30 determines, based on the distribution of the light quantity in each of the locations of the PDs 260, which has been output from the output unit 29, whether or not there is the contamination 14 between the connector 130 and the port 120. Thus, an operation time of a transmission test between the computers 12 may be reduced.

In the inspection system 10 of the first embodiment, the PDs 260 of the output unit 29 are arranged such that at least one of the PDs 260 is located in a location that each light that has been reflected by the reflection unit 22 enters when there is not the contamination 14 between the connector 130 and the port 120. Thus, whether or not there is the contamination 14 between the connector 130 and the port 120 may be determined.

In the inspection system 10 of the first embodiment, the PDs 260 of the output unit 29 are arranged such that at least one of the PDs 260 is located in a location that each light that has been reflected by the reflection unit 22 enters when there is not the contamination 14 between the connector 130 and the port 120. Thus, determination accuracy when there is the contamination 14 between the connector 130 and the port 120 may be increased.

In the inspection system 10 of the first embodiment, in the PD unit 26, the plurality of arrays each including multiple ones of the PDs 260 which are arranged in line in certain intervals in the first direction is arranged in certain intervals in the second direction. For each of the PDs 260, the determination device 30 calculates a difference between the value of an electrical signal that has been output from the PD 260 and the value of an electrical signal that is output from the PD 260 when there is not the contamination 14. Then, the determination device 30 determines, if a value calculated from the sum of the differences that have been calculated for the PDs 260 is a predetermined threshold or more, that there is the contamination 14 between the connector 130 and the port 120. Thus, whether or not there is the contamination 14 between the connector 130 and the port 120 may be determined with high accuracy.

Second Embodiment

In the first embodiment that has been described above, in the PDs 260 arranged in arrays, whether or not there is the contamination 14 is determined using the difference between the intensity of light that has been received by the PDs 260 and the intensity of light that is received by the PDs 260 when there is not the contamination 14. In contrast, in a second embodiment, based on whether or not there is regularity in an arrangement of areas of light that has entered the PD unit 26 including the plurality of PDs 260 arranged in arrays, whether or not there is the contamination 14 is determined.

Figure 14:
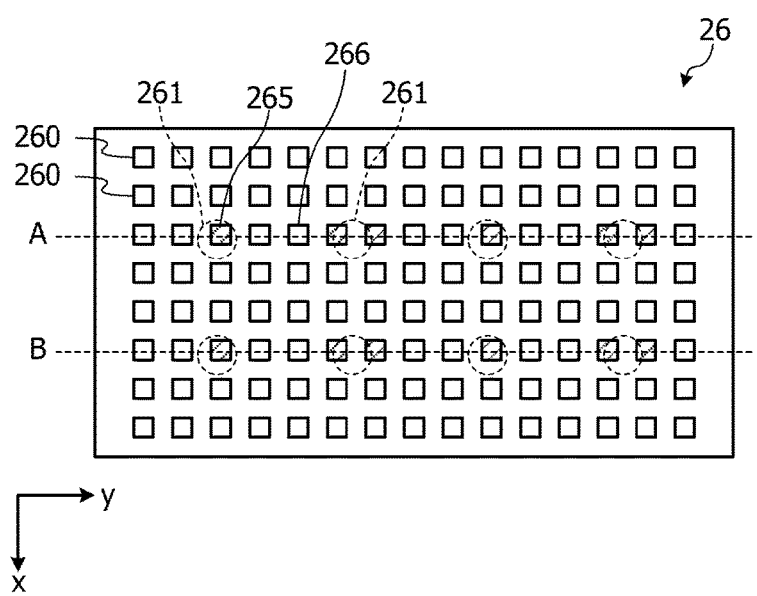
FIG. 14 is a view illustrating an example of an arrangement of PDs in a second embodiment.

FIG. 14 is a view illustrating an example of an arrangement of the PDs 260 in the second embodiment. Also, in the second embodiment, for example, as illustrated in FIG. 14, the PD unit 26 includes the plurality of PDs 260 arranged in arrays. In the PD unit 26, for example, as illustrated in FIG. 14, a plurality of arrays each including multiple ones of the PDs 260 which are arranged in line in certain intervals in a y direction in FIG. 14 is arranged in certain intervals in an x direction in FIG. 14. Information indicating the respective locations of the PDs 260 in the PD unit 26 is stored in the DB 34 in advance.

If there is not the contamination 14 between the connector 130 and the port 120, light that has been output from each optical fiber in the connector 130 and reflected by the end surface 121 of the port 120 and the reflection unit 22 enters areas 261 arranged in substantially equal intervals on the PD unit 26, for example, as illustrated in FIG. 14. The PDs 260 located in respective areas receive light that has been reflected by the reflection unit 22. In this case, the PD 260 which has received light that was reflected by the reflection unit 22 is defined as a first PD 265. The PD 260 which has not received light that was reflected by the reflection unit 22 is defined as a second PD 266. The first PD 265 is an example of a first converter. The second PD 266 is an example of a second converter.

Figure 15:
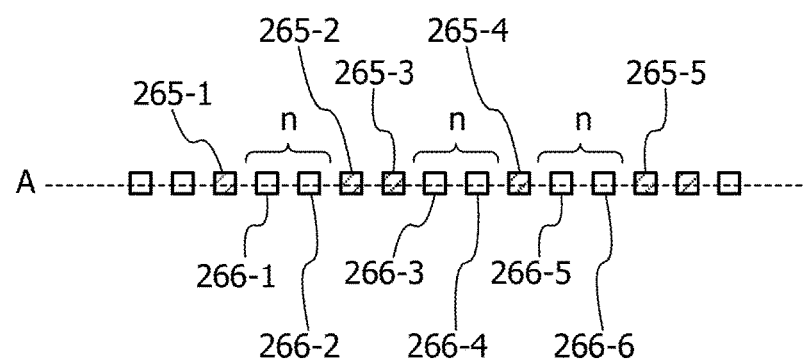
FIG. 15 is a view illustrating an example of an arrangement of first PDs and second PDs.

Among the arrays each including multiple ones of the PDs 260 which are arranged in line in certain intervals in the y direction in FIG. 14, for example, in an array in which multiple ones of the PDs 260 are arranged in a direction along a dotted line A, an arrangement of the first PDs 265 and the second PDs 266 is extracted and is illustrated, for example, in FIG. 15. FIG. 15 is a view illustrating an example of an arrangement of the first PDs 265 and the second PDs 266.

In this case, when the areas 261 that light that has been reflected by the reflection unit 22 enters are regularly arranged on the PD unit 26, for example, as illustrated in FIG. 14 and FIG. 15, there is a plurality of pairs of first PDs 265 arranged such that at least one of the second PDs 266 is located between the two first PDs 265 of each of the pairs. For example, in the example illustrated in FIG. 15, second PDs 266-1 and 266-2 are arranged between first PDs 265-1 and 265-2, and therefore, the first PDs 265-1 and 265-2 forms a pair of the first PDs 265. Similarly, the second PDs 266-3 and 266-4 are arranged between the first PDs 265-3 and 265-4, and therefore, the first PDs 265-3 and 265-4 forms a pair of the first PDs 265. Similarly, the second PDs 266-5 and 266-6 are arranged between the first PDs 265-4 and 265-5, and therefore, the first PDs 265-4 and 265-5 forms a pair of the first PDs 265. Accordingly, for example, in the array arranged in the direction along the dotted line A in FIG. 14, there is the plurality of pairs of the first PDs 265.

When the areas 261 that light that has been reflected by the reflection unit 22 enters are regularly arranged on the PD unit 26, the number n of the second PDs 266 arranged between each pair of the first PDs 265 is the same among the pairs of the first PDs 265. In the examples illustrated in FIG. 14 and FIG. 15, the number n of the second PDs 266 arranged between each of the plurality of pairs of the first PDs 265 is two. Also, in another array including multiple ones of the PDs 260 (for example, in an array in which multiple ones of the PDs 260 are arranged in a direction along a dotted line B in FIG. 14), similarly, when the areas 261 that light that has been reflected by the reflection unit 22 enters are regularly arranged on the PD unit 26, the number n of the second PDs 266 arranged between each of the pairs of the first PDs 265 is the same.

If there is the contamination 14 between the connector 130 and the port 120, light that has been output from each optical fiber in the connector 130 is reflected and scattered by the contamination 14. Then, light that has been reflected by the reflection unit 22 enters a different area 263 from the areas 261 that the light enters when there is not the contamination 14, for example, as illustrated in FIG. 16.

Figure 16:
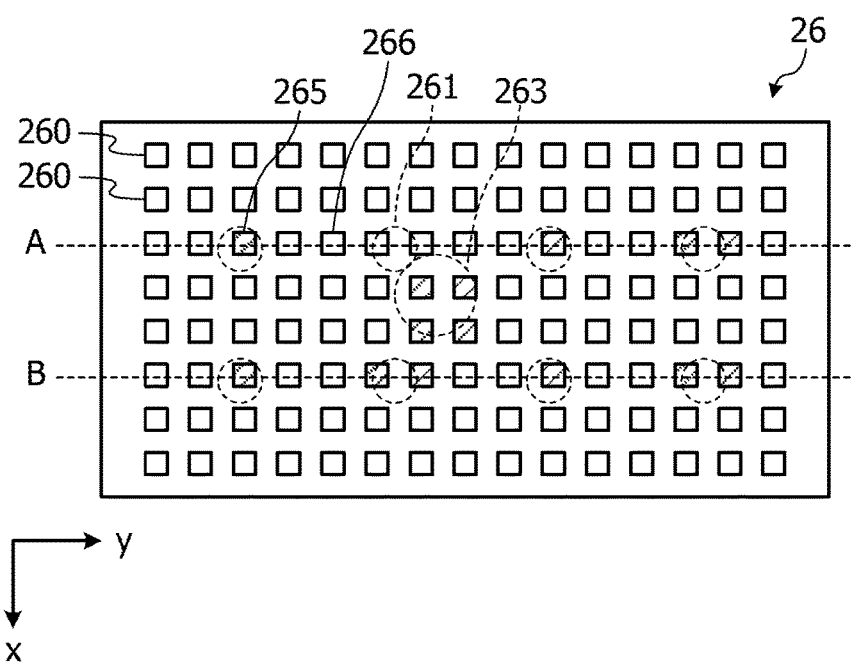
FIG. 16 is a view illustrating an example of distribution of reflected light when there is a contamination.
Figure 17:
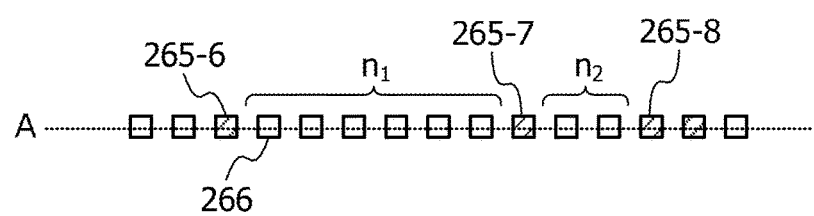
FIG. 17 is a view illustrating an example of an arrangement of first PDs and second PDs when there is a contamination.

In an array in which multiple ones of the PDs 260 are arranged in a direction along a dotted line A in FIG. 16, an arrangement of the first PDs 265 and the second PDs 266 is extracted and is illustrated, for example, in FIG. 17. FIG. 17 is a view illustrating an example of an arrangement of the first PDs 265 and the second PDs 266 when there is the contamination 14. When there is the contamination 14, although there is a plurality of pairs of the first PDs 265, among the pairs of the first PDs 265, the number of the second PDs 266 arranged between each of the pairs of the first PDs 265 differs, for example, as illustrated in FIG. 17. For example, in the example of FIG. 17, the number $n_1$ of the second PDs 266 arranged between first PDs 265-6 and 265-7 is six. The number $n_2$ of the second PDs 266 arranged between first PDs 265-7 and 265-8 is two.

Therefore, the determination processing unit 32 of the determination device 30 is enabled to determine whether or not there is the contamination 14 by determining whether or not, in an array in which there is a plurality of pairs of the first PDs 265, among the arrays each including multiple ones of the PDs 260 which are arranged in line in certain intervals in the y direction in FIG. 14, the number of the second PDs 266 arranged between each of the pairs of the first PDs 265 is the same.

In the second embodiment, for example, as illustrated in FIG. 3, two arrays of optical fibers are vertically arranged in the connector 130. Accordingly, there are three or more areas 261 of light that enters the PD unit 26 when there is not the contamination 14 in the y direction in FIG. 14, whereas there are two areas 261 in the x direction. Therefore, in the x direction, there is not an array in which there is a plurality of pairs of the first PDs 265. However, in another example in which three or more arrays of optical fibers are vertically arranged in the connector 130, there are three or more areas 261 of light that enters the PD unit 26 when there is not the contamination 14 in the x direction in FIG. 14. In the another example, which is similar to the above-described example, whether or not there is the contamination 14 may be determined by further determining, for the x direction, whether or not, in an array in which there is a plurality of pairs of the first PDs 265, the number of the second PDs 266 arranged between each pair of the first PDs 265 is the same. Thus, accuracy of determination on whether or not there is the contamination 14 may be increased.

Figure 18:
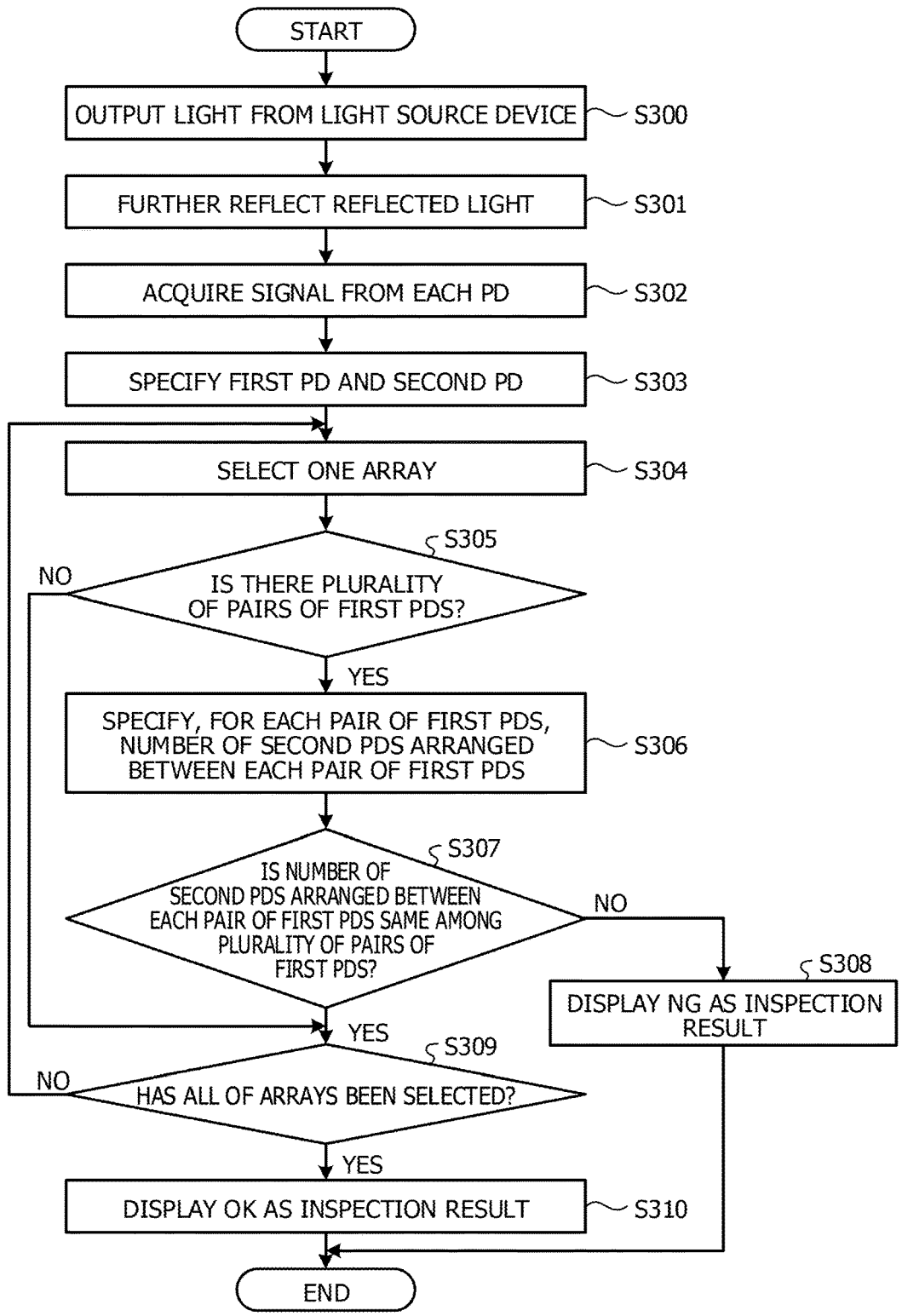
FIG. 18 is a flowchart illustrating an example of inspection processing in the second embodiment.

According to the second embodiment, in the connection check processing that has been described with reference to FIG. 10 to FIG. 13 in the first embodiment, different inspection processing from the inspection processing that has been described with reference to FIG. 13 is employed. The inspection processing in the second embodiment will be described below. FIG. 18 is a flowchart illustrating an example of inspection processing in the second embodiment.

First, in a connection state of the first connection pattern or the second connection pattern described in the corresponding one of FIG. 12A and FIG. 12B, light is output from the light source device 11 (S300). The light that has been output from the light source device 11 enters the cable 13 via the connector 130. Then, the light that has entered the cable 13 enters the detection device 20 from the connector 130 through each optical fiber in the cable 13.

As illustrated in FIG. 6, the light that has entered the detection device 20 is transmitted through the detection device 20 and is reflected by the port 120. Reflected light that has been reflected by the port 120 is further reflected by the reflection unit 22 in the detection device 20 and enters the PD unit 26 (S301).

Reflected light of each optical fiber, which has entered the PD unit 26, is converted to an electrical signal that corresponds to light quantity by each PD 260. An analog electrical signal that has been converted by each PD 260 is converted to a digital electrical signal by the ADC 27. In the second embodiment, an analog electrical signal that has been output from the PD 260 that has received reflected light is converted to a digital value (for example, "1") which indicates that the PD 260 has received light by the ADC 27. An analog electrical signal that has been output from the PD 260 that has not received reflected light is converted to a digital value (for example, "0") which indicates that the PD 260 has not received light by the ADC 27. Then, an electrical signal of each PD 260, which has been converted to a digital value, is output to the determination device 30 via the cable 200 by the I/F 28.

The determination processing unit 32 of the determination device 30 acquires an electrical signal for each PD 260, which has been output from the detection device 20, via the cable 200 and the I/F 31 (S302). Then, the determination processing unit 32 specifies, based on the value of the electrical signal of each PD 260, the PD 260 for which the digital value that indicates that the PD 260 has received light as the first PD 265. Then, the determination processing unit 32 specifies the PD 260 for which the digital value that indicates that the PD 260 has not received light as the second PD 266 (S303).

Next, the determination processing unit 32 refers to information that indicates the location of each PD 260, which is stored in the DB 34, and selects one array among the arrays each including multiple ones of the PDs 260 which are arranged in line in a certain direction (for example, the y direction in FIG. 14) (S304). Then, the determination processing unit 32 determines whether or not, in the array that has been selected in S304, whether or not there is a plurality of pairs of the first PDs 265 (S305). If there is not a plurality of pairs of the first PDs 265 (NO in S305), the determination processing unit 32 executes processing illustrated in S309.

On the other hand, if there is a plurality of pairs of the first PDs 265 (YES in S305), the determination processing unit 32 specifies, for each of the pairs of the first PDs 265, the number of the second PDs 266 arranged between the pair of the first PDs 265 (S306). Then, the determination processing unit 32 determines whether or not the number of the second PDs 266 between each of the plurality of pairs of first PDs 265 is the same among the plurality of pairs (S307).

If the number of the second PDs 266 between each of the plurality of pairs of first PDs 265 differs (NO in S307), the determination processing unit 32 determines that there is the contamination 14 between the connector 130 and the port 120. Then, the determination processing unit 32 displays NG as an inspection result on the display unit 33 (S308).

On the other hand, if the number of the second PDs 266 between each of the plurality of pairs of first PDs 265 is the same (YES in S307), the determination processing unit 32 determines whether or not the determination processing unit 32 has selected all of the arrays each including multiple ones of the PDs 260 which are arranged in line in the certain direction (S309). If there is an array that has not been selected (NO in S309), the determination processing unit 32 executes processing illustrated in S304 again.

On the other hand, if the determination processing unit 32 has selected all of the arrays each including multiple ones of the PDs 260 which are arranged in line in the certain direction (YES in S309), the determination processing unit 32 determines that there is not the contamination 14 between the connector 130 and the port 120. Then, the determination processing unit 32 displays OK as an inspection result on the display unit 33 (S310).

Using the inspection system 10 of the second embodiment, whether or not there is the contamination 14 is determined, based on regularity of an arrangement of areas on the PD unit 26, which reflected light has entered. Thus, whether or not there is the contamination 14 between the connector 130 and the port 120 may be determined with high accuracy. In the second embodiment, merely, information indicating that reflected light has been received is achieved from each PD 260, and therefore, the ADC 27 with a small bit number may be used. Thus, costs of the inspection system 10 may be reduced.

In the inspection system 10 of the second embodiment, the determination device 30 detects the first PD 265 which is the PD 260 that has received light that was reflected by the reflection unit 22 and the second PD 266 which is the PD 260 that has not received light that was reflected by the reflection unit 22. Then, the determination device 30 specifies, for each pair of the first PDs 265 that are arranged such that at least one of the second PDs 266 is located between each of the pairs of the first PDs 265, the number of the second PDs 266 arranged between each pair of the first PDs 265 in each of the arrays each including multiple ones of the PDs 260 which are arranged in line in the certain direction (for example, the y direction in FIG. 14). Then, if the number of the second PDs 266, which has been specified, differs in one of the pairs of the first PDs 265, the determination device 30 determines that there is the contamination 14 between the connector 130 and the port 120. Thus, whether or not there is the contamination 14 between the connector 130 and the port 120 may be determined with high accuracy.

Figure 19:
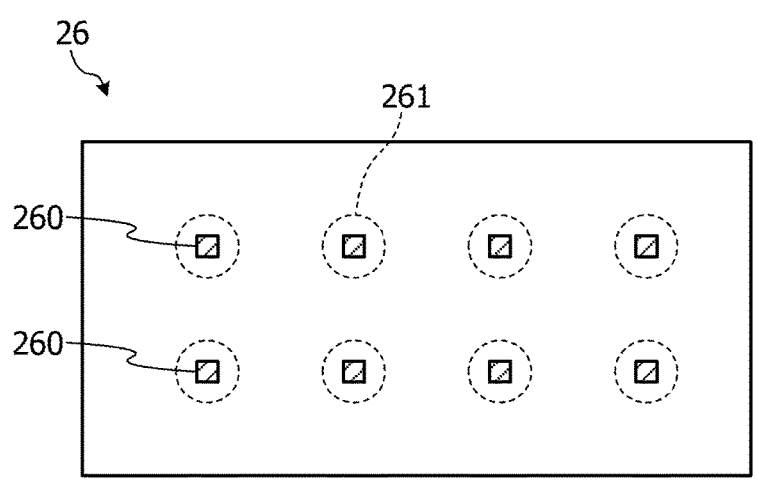
FIG. 19 is a flowchart illustrating another example of an arrangement of PDs in the second embodiment.

In the second embodiment, the PDs 260 are arranged not only in locations in the PD unit 26, which reflected light enters when there is not the contamination 14, but also in a different location from the locations in the PD unit 26, which reflected light enters when there is not the contamination 14. However, the technology disclosed herein is not limited thereto. For example, as illustrated in FIG. 19, there may be a case in which the PDs 260 are arranged in locations in the PD unit 26, which reflected light enters when there is not the contamination 14, and the PD 260 is not arranged in a different location from the locations in the PD unit 26, which reflected light enters when there is not the contamination 14, may be employed. The plurality of PDs 260 illustrated in FIG. 19 is regularly arranged on a surface of the PD unit 26.

If there is not the contamination 14, reflected light that has been reflected by the reflection unit 22 enters the areas 261 each of which includes a location in which the corresponding PD 260 is located, for example, as illustrated in FIG. 19. Each of the PDs 260 is regularly arranged on the surface of the PD unit 26. Therefore, when reflected light enters the PD unit 26 in a regular arrangement, the reflected light is received in all of the PDs 260.

Figure 20:
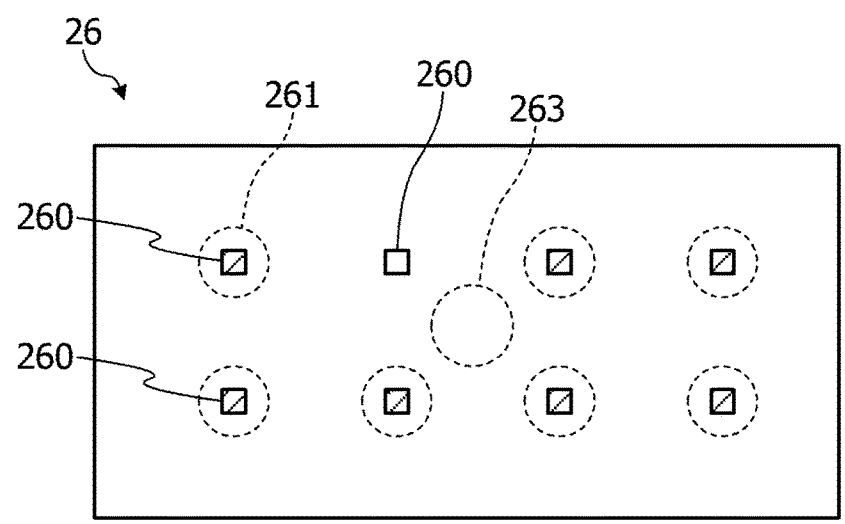
FIG. 20 is a view illustrating an example of distribution of reflected light when there is a contamination.

On the other hand, if there is the contamination 14, light from the optical fibers is reflected and scattered by the contamination 14. Therefore, for example, as illustrated in FIG. 20, the reflected light that has been reflected by the reflection unit 22 enters the area 263 that is different from the areas 261 on the PD unit 26, which light enters when there is not the contamination 14. Therefore, if there is the contamination 14, the reflected light is not received in some of the PDs 260. In the example of FIG. 20, ones of the PDs 260, which are hatched, indicate the PDs 260 that have received the reflected light. One of the PDs 260, which is not hatched, indicates the PD 260 that has not received the reflected light.

Therefore, in the examples of FIG. 19 and FIG. 20, if the reflected light has been received in all of the PDs 260, the determination processing unit 32 determines that there is not the contamination 14. Then, the determination processing unit 32 determines, if the reflected light is not received at least in some of the PDs 260, that there is the contamination 14.

Figure 21:
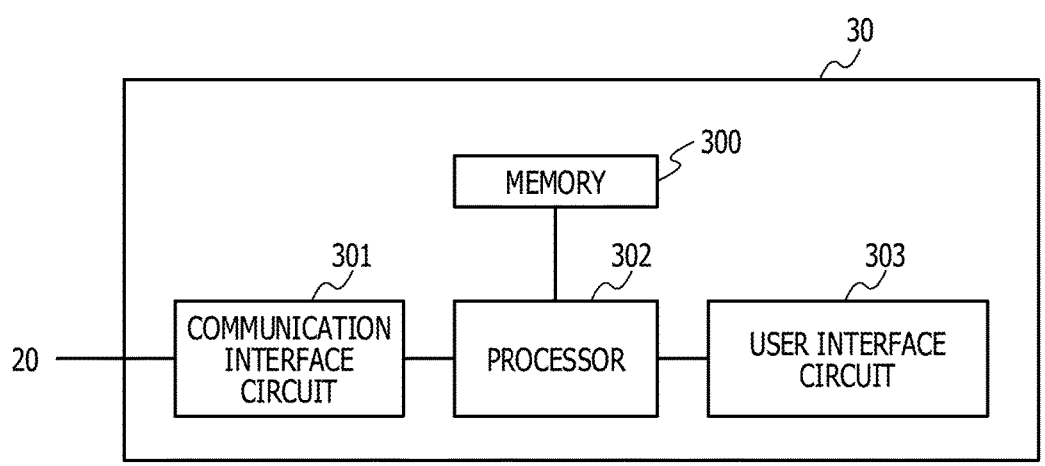
FIG. 21 is a block diagram illustrating an example of a hardware of a determination device.

The determination device 30 in the first embodiment or the second embodiment, which have been described above, is realized, for example, by a hardware illustrated in FIG. 21.

FIG. 21 is a block diagram illustrating an example of a hardware of the determination device 30. For example, as illustrated in FIG. 21, the determination device 30 includes a memory 300, a communication interface circuit 301, a processor 302, and a user interface circuit 303.

The communication interface circuit 301 is an interface that performs a communication with the detection device 20 via the cable 200. The communication interface circuit 301 realizes, for example, a function of the I/F 31. The user interface circuit 303 is an interface, such as, for example, a display, a keypad, or the like, which notifies an operator of the determination device 30 or the like of an output form the processor 302, and is used by the operator to input data to the processor 302. The user interface circuit 303 realizes, for example, a function of the display unit 33.

In the memory 300, various types of programs and data, which are used to realize, for example, a function of the determination device 30, or the like, are stored. The value of an electrical signal of each PD 260 when there is not the contamination 14 between the connector 130 and the port 120 and information, such as a threshold used for determining whether or not there is the contamination 14, or the like, are stored in the memory 300 in advance. The processor 302 realizes, for example, each function of the determination device 30 using data in the memory 300 by executing a program that has been read out from the memory 300.

There may be a case in which not all of the programs, data, or the like in the memory 300 is stored in the memory 300 from beginning. For example, a configuration in which a program, data, or the like is stored in a portable recording medium, such as a memory card or the like, which is inserted in the determination device 30 and the determination device 30 acquires the program, data, or the like from the potable recording medium to execute the program, data, or the like may be employed. Also, a configuration in which the determination device 30 acquires, from another computer, a server device, or the like, in which a program, data, or the like is stored, the program via a wireless communication line, a public network, the Internet, a LAN, a WAN, or the like, to execute the program may be employed.

The technology disclosed herein is not limited to each of the embodiments that have been described above and various modifications may be made to those embodiments without departing from the scope of the gist of the present disclosure.

For example, in the detection device 20 of the first embodiment that has been described above, the reflection unit 22 is arranged so as to be oblique relative to a path of light that is output from an optical fiber or enters the optical fiber between the light guide unit 21 and the light guide unit 23, but the technology disclosed herein is not limited thereto. For example, a configuration in which the light guide unit 21 and the light guide unit 23 that have different refractive indexes are joined together at a plane formed obliquely relative to the path of light that is output from an optical fiber or enters the optical fiber may be employed. In this configuration, a part of light that has been reflected by the end surface 121 of the computer 12 may be caused to be also reflected on a boundary surface between the light guide unit 21 and the light guide unit 23 and enter the PD unit 26. The boundary surface between the light guide unit 21 and the light guide unit 23 is an example of a reflection unit.

In the first embodiment that has been described above, the determination processing unit 32 determines, for each PD 260, whether or not there is the contamination 14, based on a difference between the value of an electrical signal that has been output from the detection device 20 and the value of an electrical signal, which is stored in the DB 34. However, the technology disclosed herein is not limited thereto. For example, an electrical signal that indicates light quantity in each of the locations of the PDs 260 may be calculated as a feature vector and whether or not there is the contamination 14 between the connector 130 and the port 120 may be determined using the calculated feature vector.

For example, if there is not the contamination 14 between the connector 130 and the port 120, some patterns of an electrical signal that has been output from each PD 260 are collected in advance and, for each of the collected patterns, a first feature vector is calculated. Then, the plurality of first feature vectors, which have been calculated, is stored in the DB 34. Similarly, for example, if there is the contamination 14 between the connector 130 and the port 120, some patterns of an electrical signal that has been output from each PD 260 are collected in advance and, for each of the collected patterns, a second feature vector is calculated. Then, the plurality of second feature vectors, which have been calculated, is stored in the DB 34.

In inspection processing, the determination processing unit 32 calculates a third feature vector, based on an electrical signal that has been output form the detection device 20. Then, the determination processing unit 32 reads out the plurality of first feature vectors and the plurality of second feature vectors from the DB 34. Then, for example, as illustrated in FIG. 22, the determination processing unit 32 determines whether or not there is the contamination 14 between the connector 130 and the port 120 by determining whether or not the calculated third feature vector 51 belongs to a range of a class of the first feature vectors.

Figure 22:
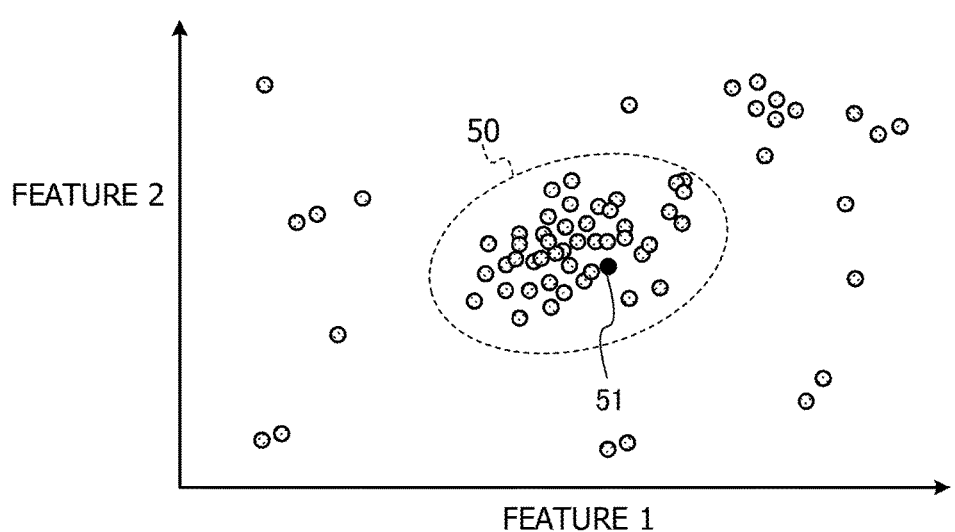
FIG. 22 is a graph illustrating an example of feature vector classification.

FIG. 22 is a graph illustrating an example of feature vector classification. In FIG. 22, as an example, a distribution of points that correspond to feature vectors that are represented by two feature amounts is illustrated. Whether the third feature vector 51 is classified to a class to which the first feature vectors belong or a class to which the second feature vectors belong may be determined using an algorithm, such as, for example, "K-means", "a support vector machine", or the like.

If it is determined that the third feature vector 51 belongs to the class of the first feature vectors, the determination processing unit 32 additionally stores the third feature vector as the first feature vector in the DB 34. On the other hand, if it is determined that the third feature vector 51 belongs to the class of the second feature vectors, the determination processing unit 32 additionally stores the third feature vector as the second feature vector in the DB 34. Thus, by repeating the inspection processing, samples of the first feature vectors and the second feature vectors are increased and the accuracy of processing of determining whether or not there is the contamination 14 between the connector 130 and the port 120 is increased.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An inspection system comprising:
a connector coupled to a plurality of optical fibers:
a detection device arranged between the connector and a port of a computer and configured to guide a light passed through the plurality of optical fibers and output from the connecter, in a first direction to the port and in a second direction to a plurality of diodes included in the detection device; and
a determination device coupled to the detection device and configured to determine whether there is a contaminant between the connector and the port, the plurality of diodes are configured to convert the light to an electrical signal indicating intensity and distribution of the light, and
the determination device includes a processor configured to determine whether there is the contaminant between the connector and the port, based on the intensity and distribution of the light, which are indicated by the electrical signal;
wherein the processor is configured to:
detect first diodes that have received the light that was reflected by the contact surface among the plurality of diodes and second diodes that have not received the light that was reflected by the contact surface among the plurality of diodes,
specify, in each of arrays of ones of the plurality of diodes, which are arranged in lines in the first direction, for each pair of the first diodes between which at least one of the second diodes is arranged, the number of the second diodes that are arranged between each pair of the first diodes, and
determine that the contaminant is between the connector and the port when the number of the specified second diodes is different among the pairs of the first diodes.

2. The inspection system according to claim 1, wherein the detection device includes a housing including two members having different refractive indexes, and a contact surface of the two members is arranged so as to be oblique to an optical path of the light that is output from each of the plurality of optical fibers.

3. The inspection system according to claim 1, wherein the contact surface reflects the light that has been output from each of the plurality of optical fibers and the light that has been reflected by the port to cause the lights to enter the plurality of diodes.

4. The inspection system according to claim 3, wherein the plurality of diodes is arranged such that at least one of the diodes is located in a location which the light that has been reflected by the contact surface enters when there is not the dart between the connector and the port.

5. The inspection system according to claim 3, wherein the plurality of diodes is arranged such that the light has been reflected by the contact surface enters through at least one of the plurality of diodes where the contaminant is located.

6. The inspection system according to claim 1, wherein the detection device further includes a converter that converts the electrical signal from an analog signal to a digital signal.

7. The inspection system according to claim 1, wherein the processor is configured to:
calculate, for each of the plurality of diodes, a difference between a value of an electrical signal that has been output from the diode and a value of an electrical signal that is output from the diode when there is not dart, and determine that the contaminant is between the connector and the port, when a sum of the differences that have been calculated for the plurality of diodes is a threshold or more.

8. The inspection system according to claim 1, wherein the plurality of diodes is arranged in a matrix in certain intervals in the first direction and the second direction that is different from the first direction.

9. The inspection system according to claim 8, wherein the processor is configured to:
   calculate, based on the intensity of the light for each of the locations of the plurality of diodes, a feature vector of the electrical signal, and
   determine whether the contaminant is between the connector and the port, based on the degree of similarity to the feature vector when the contaminant is not between the connector and the port and the degree of similarity to the feature vector when the contaminant is between the connector and the port.

10. An inspection method executed by an inspection system including a connector coupled to a plurality of optical fibers, a detection device arranged between the connector and a port of a computer, and a determination device coupled to the detection device and configured to determine whether a contaminant is between the connector and the port, the inspection method comprising:
   guiding, by the detection device, a light, passed through the plurality of optical fibers and output from the connecter, in a first direction to the port and in a second direction to a plurality of diodes included in the detection device;
   converting, by the plurality of diodes the light to an electrical signal indicating intensity and distribution of the light; and
   determining, by a processor included in the determination device, whether the contaminant is between the connector and the port, based on the intensity and distribution of the light, which are indicated by the electrical signal;
   wherein the processor is configured to:
   detect first diodes that have received the light that was reflected by the contact surface among the plurality of diodes and second diodes that have not received the light that was reflected by the contact surface among the plurality of diodes,
   specify, in each of arrays of ones of the plurality of diodes, which are arranged in lines in the first direction, for each pair of the first diodes between which at least one of the second diodes is arranged, the number of the second diodes that are arranged between each pair of the first diodes, and
   determine that the contaminant is between the connector and the port when the number of the specified second diodes is different among the pairs of the first diodes.

11. The inspection method according to claim 10, wherein the detection device includes a housing including two members having different refractive indexes, and
   a contact surface of the two members is arranged so as to be oblique to an optical path of the light that is output from each of the plurality of optical fibers.

12. The inspection method according to claim 10, wherein the contact surface reflects the light that has been output from each of the plurality of optical fibers and the light that has been reflected by the port to cause the lights to enter the plurality of diodes.

13. The inspection method according to claim 12, wherein the plurality of diodes is arranged such that the light has been reflected by the contact surface enters through at least one of the plurality of diodes where the contaminant is located.

* * * * *